United States Patent [19]

Djurickovic

[11] 4,046,875

[45] Sept. 6, 1977

[54] ATTENUATED TGE VIRUS

[75] Inventor: Slobodan M. Djurickovic, Middletown, Md.

[73] Assignee: Richardson-Merrell Inc., Wilton, Conn.

[21] Appl. No.: 751,902

[22] Filed: Dec. 17, 1976

Related U.S. Application Data

[63] Continuation-in-part of Ser. No. 595,621, July 14, 1975, abandoned.

[51] Int. Cl.² ............................ A61K 39/12; C12K 9/00
[52] U.S. Cl. ............................................ 424/89; 195/1.3
[58] Field of Search ............................ 195/1.3; 424/89

[56] References Cited

U.S. PATENT DOCUMENTS

| | | | |
|---|---|---|---|
| 3,585,108 | 6/1971 | Welter | 195/1.3 |
| 3,704,203 | 11/1972 | Welter | 195/1.3 |

*Primary Examiner*—Sam Rosen
*Attorney, Agent, or Firm*—George W. Rauchfuss, Jr.; Eugene O. Retter

[57] ABSTRACT

A TGE virus is attenuated in organ culture of the colon of swine. After a number of passages, the resulting attenuated virus, if administered to swine will not seriously damage the villi of the small intestine, so that absorption of protein and other vital materials is not seriously hampered. The swine may suffer slight side effects, but are then immune to virulent TGE virus which is normally fatal to piglets.

12 Claims, No Drawings

ATTENUATED TGE VIRUS

RELATED APPLICATIONS

This application is a continuation-in-part of earlier copending application Ser. No. 595,621, filed on July 14, 1975, now abandoned.

BACKGROUND OF THE INVENTION

1. Field of the Invention

The invention relates to the production of an attenuated virus of transmissible gastroenteritis of swine (TGE), the vaccine resulting from said attenuated virus and the administration of said vaccine.

2. The Prior Art

Recently published reports on the mechanism of passive immunity against TGE virus, indicated that there is a marked advantage of oral in contrast to parenteral vaccination of pregnant sows for providing immunity to suckling piglets. The secretion of TGE antibodies of the immunoglobulin (IgA) class in the milk as a result of oral but not parenteral (except intramammary route of vaccination) vaccination was considered to be the most appropriate explanation. Attempts to stimulate the production of such antibodies in the milk have been the most successful as a consequence of an infection of the gastrointestinal tract with natural or attenuated virus. The explanation has been proposed that, after antigenic stimulation of the gastrointestinal tract of pregnant sows with live attenuated organ-cultured TGE virus, sensitized immunocytes from the lamina propria relocate and colonize the mammary gland where antibodies of the secretory IgA class are synthesized and secreted in colostrum and in the milk.

TGE vaccines that were available have not been completely satisfactory for controlling the disease in the field and of very limited value. These vaccines did not produce adequate passive immunity. The TGE virus modified by numerous passages on pig kidney tissue culture can rapidly be reversed in its virulence in one to three back passages. Thus, it was hard to achieve the right type of attenuation which will satisfy both safety and immunogenicity.

SUMMARY OF THE INVENTION

According to the invention, a TGE virus is attenuated by culturing on pig colon cultures. After a number of passages the virus when administered to swine will not seriously affect the small intestine so that the villi of the small intestine will not be damaged and the absorption of protein and other vital elements is not prevented. There are mild side effects which, however, are not fatal as TGE ordinarily is.

The development of safe and antigenically competent vaccine requires new methods which will induce good propagation and attenuation of TGE virus. With this in mind it was decided to propagate and attenuate the TGE virus in colon organ culture of pigs.

The studies carried out up to present time showed a great deal of difference between the originally isolated TGE virus and the colon organ cultured attenuated virus. The differences are:

a. Colon organ cultured TGE virus passaged 1 to 15 times on colon organ cultures according to this invention show cytopathic effect (CPE) in a very first Fetal Pig Kigney (FPK) cell culture passage. However, the originally isolated Ontario strain TGE virus needed five to eight (FPK) cell culture passages to become cytopathogenic.

b. The colon organ cultured fifteenth level passage TGE virus and its five subsequent (FPK) cell culture passages produced diarrhea in baby pigs only after a prolonged incubation period (5-7 days); the diarrhea lasted 2-3 days; there were no signs of severe dehydration and emaciation. There was no mortality on first or second passage in piglets at culture passage level 5 and above. Originally isolated TGE virus is highly pathogenic for baby piglets, has a short incubation period (18-36 hours) and produces severe dehydration and emaciation and generally about 100% mortality.

c. Villous atrophy is confined to the colon in all piglets inoculated with colon organ cultured TGE virus at least as early as the 15th level and possibly earlier. The small intestines were normal. The originally isolated Ontario strain TGE virus produced severe villous atrophy in the small intestines, mainly the jejunum and the ileum, which causes malabsorption and consequently generally about 100% mortality.

DESCRIPTION OF THE PREFERRED EMBODIMENTS

Source of the TGE Virus of Pigs

Ontario V-52 Strain TGE virus was isolated from an outbreak of highly infectious gastroenteritis of pigs. Portions of the small intestine and its contents were placed in a Ten Broeck grinder with approximately nine parts of phosphate buffered saline (PBS) pH 7.4 containing 500 units of penicillin per ml., 500 mg of streptomycin per ml. and 500 units of mycostatin per ml. The material was ground under a bacteriological hood equipped with an ultraviolet sterilizing lamp. The coarse particulate matter was removed by centrifugation at 1,000 g for 30 minutes at 4° C. and the supernatant was recentrifuged at 10,000 g for 30 minutes at 4° C. to remove bacteria. The supernatant from this second centrifugation was frozen and stored at −70° C. until attenuation was started on an organ culture of pig colon. Bacterial sterility was tested by inoculation or thioglycollate, tryptic soy broth and blood agar. The inoculated cultures were incubated in aerobic and anaerobic conditions. The Ontario V-52 strain virus was identified as TGE virus by the neutralization test, fluorescent antibody staining, electron microscopy and production of the specific disease in 3 day old germ-free piglets.

Organ Culture Technique

Ninety-to-100-day pig fetuses were delivered by hysterectomy into a surgical isolator. The colon samples were removed from all of the fetuses within 30 minutes of delivery. The samples were collected in a medium of 90% balanced salt solution (BSS) and 10% fetal calf serum (FCS), were washed three times, and were cut into pieces 2 mm². The colon pieces were placed mucosa side upward on scratched areas in the bottom of a 80 mm plastic Petri dish. The pieces adhered strongly to the four 3 mm² areas that had been prepared by scratching the surface with a sterile scalpel blade. A nutrient Basal Medium Eagle (BME) was used with 0.5% bovine plasma albumen (adjusted to pH 7.4 with 1N NaOH) and 10% FCS. The medium contained 250 units of penicillin and mycostatin per ml. and 250 mg of streptomycin per ml. The medium was added just to the level of the top of the colon fragments. Villous activity was observed by means of a dissecting microscope, and only cultures showing strong villous movement were infected with Ontario V-52 strain TGE virus. The colon organ cultures were infected with 0.1 ml of the described bacteria-free supernatant.

After adsorption for 3 hours at 37° C., the cultures were washed 3 times with Hank's BSS and fresh Eagle's BME medium was added. The Petri dish colon cultures were incubated at 39° C. in a humidified incubator with 5% $CO_2$ in air. A sample of medium was removed from the organ culture at 2 days post inoculation (p.i.) and was frozen at −70° C. for the next passage on organ culture. At 3 days p.i. and at 3 day intervals thereafter the medium was removed and replaced with fresh medium.

Five consecutive passages were made by the same method. The highest titer of the TGE virus and the change in the condition of the villi occurred at 48 hr. p.i.

The TGE virus titer peaked at 48 hours p.i. through organ culture passage five. The titer peak occurred at 24 hours p.i. in the next 10 passages in colon organ culture.

Virus titrations were performed in fetal pig kidney (FPK) cultures. The endpoint was determined by reading CPE. Titers for the 24 hour harvest of colon culture passages 5 to 15 were as follows.

Table 1

| Colon Organ Culture Passage No. | Titer at 24 hours p.i. |
|---|---|
| 5 | $10^{4.8}$ $TCID_{50}$/ml |
| 6 | $10^{6.8}$ $TCID_{50}$/ml |
| 7 | $10^{7.0}$ $TCID_{50}$/ml |
| 8 | $10^{7.2}$ $TCID_{50}$/ml |
| 9 | $10^{7.0}$ $TCID_{50}$/ml |
| 10 | $10^{7.2}$ $TCID_{50}$/ml |
| 11 | $10^{7.0}$ $TCID_{50}$/ml |
| 12 | $10^{6.8}$ $TCID_{50}$/ml |
| 13 | $10^{7.2}$ $TCID_{50}$/ml |
| 14 | $10^{6.8}$ $TCID_{50}$/ml |
| 15 | $10^{7.0}$ $TCID_{50}$/ml |

Cell Culture

Fetal pig kidney (FPK) cultures were prepared from kidneys of 100–105 day old fetuses removed by hysterectomy from specific pathogen free (SPF) sows. The sows originated from a certified SPF herd, free of *Mycoplasma pneumonia*, *Atrophic rhinitis*, Leptospirosis, Brucellosis and TGE. Fetuses were removed from the uterus in a sterile plastic isolator and the kidneys were removed and tissue prepared by trypsinization procedure routinely used with primary tissue culture. This included rinsing finely minced tissue with serial changes of cold PBS containing Kanamycin (100 mg per ml.). Cells were dispersed by overnight trypsinization at 4° C. Approximately 50 ml of trypsin was added per pair of kidneys and was stirred continuously with a magnetic stirrer. The dispersed cells were filtered through four layers of gauze and sedimented in a refrigerated centrifuge (4° C.) at 1000 rpm for 15 minutes. The packed cells were diluted 1:400 with growth medium which contained Minimum Essential Medium (MEM) Eagle's with Hank's salts, FCS 7%, 100 units of penicillin, 100 mg. of streptomycin and 100 units of Fungizone per ml.

Plastic tissue culture flasks (25 cm²) were planted with 10 ml of the cell suspension in growth medium. Cells were harvested at 5 to 6 days with cell sheets at near confluency. Cells were removed from the bottles with 0.25% trypsin, rinsed with cold medium, suspended in freezing medium and stored in liquid nitrogen in 1 or 2 ml aliquotes. The freezing medium contained MEM Hank's, 7.5% dimethyl sulfoxide and 5% FCS.

Monolayers of FPK of cells for purposes of propagation and titrations of TGE virus were prepared by a 1:150 dilution of the frozen cells with growth medium. Tubes were prepared with 1 ml cell suspension per tube. The growth medium was removed and replaced with fresh medium on the third or fourth day, which replacement medium contained additional sodium bicarbonate at the final concentration of 0.09% by volume based on the volume of the culture medium. Cell sheets usually were ready for inoculation in five or six days.

Eagle's MEM medium with Earle's salts and about 1–2% FCS was used as maintenance medium.

Organ-cultured virus of the 15th passage was used for inoculation of FPK cell cultures. However, earlier passaged organ-cultured virus from the 5 to 15 passage could be used. The virus (inoculum—1% of medium) was adsorbed for 1 hour at room temperature, washed 3 times with Hank's BSS, then Eagle's MEM with about 1 to 2% FCS was added and incubated at 39° C. A pronounced CPE appeared after 24 to 48 hours of incubation, and the virus was harvested and stored at −70° C. Five consecutive passages in FPK cell culture were made under the same conditions. Titers for passage 1 to 5 on FPK cell cultures at 24 hour harvest of sample were as follows:

Table 2

| FPK Passage No. | Titer |
|---|---|
| 1 | $10^{7.0}$ $TCID_{50}$/ml |
| 2 | $10^{6.0}$ $TCID_{50}$/ml |
| 3 | $10^{8.0}$ $TCID_{50}$/ml |
| 4 | $10^{6.5}$ $TCID_{50}$/ml |
| 5 | $10^{7.5}$ $TCID_{50}$/ml |

Safety Test

TGE virus from the fifteenth organ culture passage and the five FPK cell culture passages was tested by oral inoculation of two 3-day-old piglets for each passage. Each piglet received a 2 ml dose. The observation period was 12 days. One piglet was killed on day seven post inoculation (p.i.) and a bacteria free supernatant was prepared from the small and large intesting for back passage. Five serial back passages in piglets were made with each of the virus passages tested. All unsacrificed piglets survived 12 days post inoculation. They had mild water diarrhea which appeared on the fifth day p.i. and lasted 3 to 4 days. There were no signs of severe dehydration or emaciation.

With respect to the sacrificed piglets the following observations were made:

Gross Pathological Observation — Only the large intestines contained yellow fluid and some curdled milk. The large intestinal walls were thinner and atonic. The small intestines appeared normal.

Dissecting Microscope Examination of the Intestinal Mucosa — The mucosa duodenum, jejunum and ileum appeared essentially normal. Changes which consisted of shortening and broadening of the villi were found in the colon. The alteration of the colon mucosa was a constant finding in infected pigs with organ-cultured virus of the 15th passage, and first to fifth passage of the virus on FPK cell culture.

For actual vaccination, the attenuated virus would generally be administered orally to the sow in an amount of about 2 cc.

What is claimed is:

1. An attentuated live transmissible gastroenteritis (TGE) virus vaccine for swine comprising an attentuated live transmissable gastroenteritis virus and a pharmaceutically acceptable carrier, wherein the TGE virus has been attenuated by passaging virulent TGE virus on pig colon organ culture for at least five serial passages; said vaccine being suitable for oral administration to sows and said vaccine being further characterized by leaving the villi of the small intestines of piglets, to which the vaccine has been administered, undamaged and adsorption of protein by said villi is not prevented.

2. The vaccine of claim 1 wherein the attentuated TGE virus has been passaged in fetal pig kidney cell tissue cultures following the passaging in pig colon organ cultures.

3. The vaccine of claim 2 wherein the attentuated TGE virus has been passaged for at least 15 serial passages in pig colon organ cultures and then passaged from about one to five serial passages in fetal pig kidney cell tissue cultures.

4. A process for the preparation of attenuated live TGE virus composition adapted for introduction into the body of swine in order to confer immunity against subsequent infection by virulent TGE swine virus comprising:
   a. inoculating a culture of pig colon organ cells in a maintenance culture medium solution with a virulent strain of TGE virus,
   b. allowing the virus to multiply in said culture for one or more days, and
   c. separating the culture medium infected with said virus from the colon organ culture,
   d. inoculating fresh colon organ cultures with virus from (b),
   e. repeating steps (b), (c) and (d) for at least five passages until a virus infected culture medium having an average titer of the virus of at least $10^{7.0}$ TCID$_{50}$ per ml by a cytopathic effect test in tubes of fetal pig kidney cell cultures is obtained,
   f. separating the colon organ cells from the culture medium and harvesting the resulting virus-containing culture medium.

5. A process for the preparation of attenuated live TGE virus composition according to claim 4 wherein steps (b), (c) and (d) are repeated at least 15 times.

6. A process for the preparation of attenuated live TGE virus composition according to claim 5 wherein the resulting virus-containing culture medium of step (f) is thereafter passaged in fetal pig kidney cell tissue cultures.

7. A process for the preparation of attenuated live TGE virus composition according to claim 6 wherein the resulting virus containing culture medium of step (f) is passaged in fetal pig kidney cell cultures for about 1 to 5 serial passages.

8. A process for the preparation of attentuated live TGE virus vaccine comprising the steps of introducing virulent TGE virus strain into an organ culture maintenance medium containing viable cells of pig colon, incubating said organ culture medium by tissue culture techniques at 39° C. for at least five serial passages, removing the colon cells and then harvesting the resulting attenuated live TGE virus-containing solution.

9. A method of conferring immunitiy to piglets against transmissible gastroenteritis virus of swine by administering to pregnant sows an antivirally effective amount of the live attenuated transmissible gastroenteritis virus vaccine of claim 2.

10. A method of conferring immunity to piglets against transmissible gastroenteritis virus of swine by administering to pregnant sows an antivirally effective amount of the live attentuated transmissible gastroenteritis virus vaccine of claim 3.

11. The method of claim 9 wherein the virus vaccine is orally administered to the pregnant sow.

12. The method of claim 10 wherein the virus vaccine is orally administered to the pregnant sow.

* * * * *